(12) United States Patent
Primeau et al.

(10) Patent No.: US 8,641,194 B2
(45) Date of Patent: Feb. 4, 2014

(54) SYSTEM FOR IN VIVO ANALYSIS OF TEAR FILM IN THE HUMAN EYE VIA PHASE SHIFTING INTERFEROMETRY

(75) Inventors: Brian C. Primeau, Tucson, AZ (US); John E. Greivenkamp, Jr., Tucson, AZ (US); James William Haywood, Fleming Island, FL (US); Gregory A. Williby, St. Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 177 days.

(21) Appl. No.: 13/238,507

(22) Filed: Sep. 21, 2011

(65) Prior Publication Data
US 2013/0010257 A1 Jan. 10, 2013

Related U.S. Application Data

(60) Provisional application No. 61/505,785, filed on Jul. 8, 2011.

(51) Int. Cl.
*A61B 3/10* (2006.01)
*A61B 3/14* (2006.01)

(52) U.S. Cl.
CPC ........................................ *A61B 3/14* (2013.01)
USPC ......................................... 351/206; 351/205

(58) Field of Classification Search
USPC .................................................. 351/205, 206
See application file for complete search history.

(56) References Cited

U.S. PATENT DOCUMENTS

2011/0237999 A1* 9/2011 Muller et al. ................... 604/20

* cited by examiner

*Primary Examiner* — Mahidere Sahle
(74) *Attorney, Agent, or Firm* — Carl J. Evens

(57) ABSTRACT

An in vivo method of characterizing dynamic tear films has been developed using a near infrared phase-shifting interferometer. This interferometer continuously measures light reflected from the tear film, allowing precision analysis of the dynamic surface topography. Movies showing the tear film behavior may be generated along with quantitative metrics describing the tear film surface as it changes in time.

18 Claims, 5 Drawing Sheets

FIG. 5
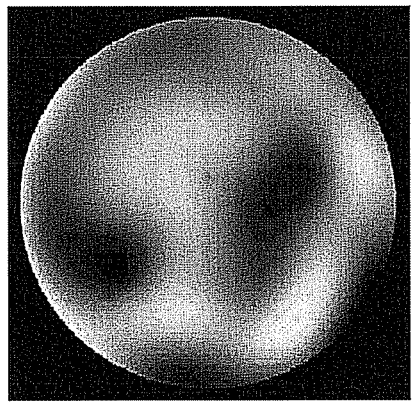
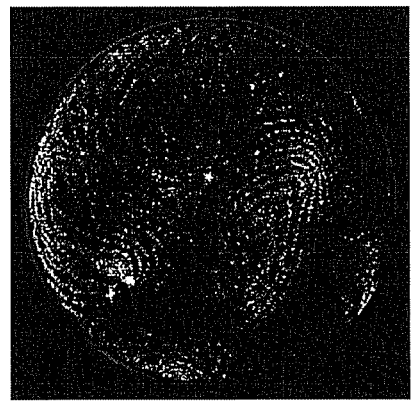
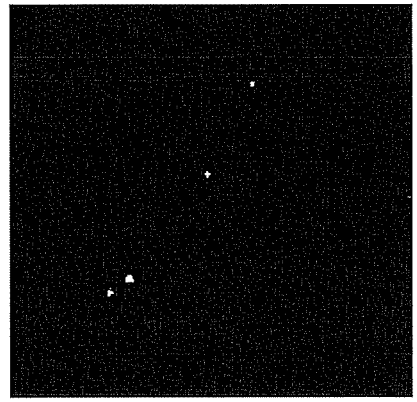
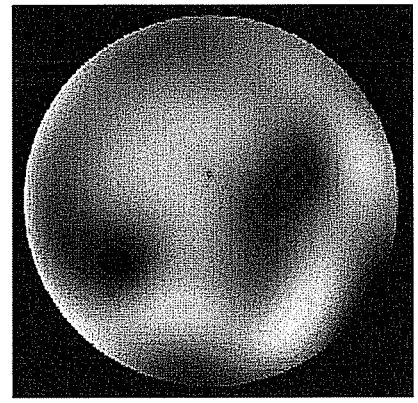

SYSTEM FOR IN VIVO ANALYSIS OF TEAR FILM IN THE HUMAN EYE VIA PHASE SHIFTING INTERFEROMETRY

CROSS REFERENCE TO RELATED APPLICATIONS

This patent application claims the benefit of U.S. Provisional Patent Application Ser. No. 61/505,785 filed Jul. 8, 2011.

BACKGROUND OF THE INVENTION

1. Field of the Invention

The present invention is directed to optical metrology, and more particularly to a system for measuring tear film dynamics and material interaction of tears in the human eye using phase shifting interferometry.

2. Discussion of the Related Art

In the human eye, the tear film is distributed over the cornea to create a smooth surface. Since the largest refractive index difference in the eye occurs at the air-to-tear film interface, this surface contributes a majority of the eye's optical power. In addition to its optical properties, the tear film serves to lubricate the eye, and in general keep it in a healthy state.

When a person blinks, a new tear film is distributed on the cornea. After the blink, the tear film stabilizes. At this point in time, the tear film is as smooth as it will ever be. Essentially, this is in the optimal state for the tear film. If no blinking occurs, the tear film normally begins to breakup over a period of time ranging from about four (4) to about fifteen (15) seconds. During the breakup, the tear film becomes turbulent and begins to dry up in places. This may cause decreased visual acuity along with discomfort. Non-uniformity in the tear film may also lead to refraction errors caused by light scatter.

When a contact lens is placed on the eye, layers of tear film form both between the contact lens and the cornea and over the anterior contact lens surface. Proper distribution of the tear film is critical to achieving a comfortable lens fit and vision improvement, so lens materials must be designed to have a proper wetability. While some lens materials provide improvements such as increased oxygen permeability, their effects on tear film distribution are unknown. Presently, the lens must be tested in vivo during clinical trials where qualitative and only semi-quantitative tear film analysis methods, such as using fluorescein eye stain and slit lamp imaging, are used to evaluate tear film evolution and breakup. However, these methods lack the sensitivity and resolution to fully observe tear film dynamics. Therefore, a high resolution method of measuring tear film topography in vivo is desired.

In current practice, one method of tear film examination relies on instilling fluorescein in an eye and examining the fluorescing light with a slit lamp or similar instrument. In this method, the examination is completely subjective and no quantitative analysis of the tear film can be made. Furthermore, introducing a foreign element into the eye could alter the tear film itself.

Another current method involves using a corneal topographer where a ring or grid pattern is reflected off of the tear film and their deviations from the desired shape provide information about the tear film topography. These systems have low sensitivity and spatial resolution and are not capable of measuring relatively small artifacts in the tear film.

Some research has been done using shearing interferometry to measure the tear film topography. In this method, the wavefront reflected from the tear film is split and shifted in order to be interfered with itself. While this provides higher sensitivity and resolution than previously discussed methods, its sensitivity resolution and are less than what is required to provide early identification of tear film artifacts. Also, to our knowledge, no attempt has been made to convert the shearing interferometry data to an actual surface topography. Instead, Fourier analysis is performed on the fringe patterns and their changes used to quantify changes to the tear film.

Accordingly, there exists a need for developing a system and methodology for analyzing tear film dynamics in the human eye, in vivo, and then using this information to calculate the tear film's topographic surface profile with better accuracy and resolution than the previously described systems.

SUMMARY OF THE INVENTION

The present invention overcomes many of the disadvantages associated with the current methods and systems for the evaluation of tear film dynamics in the human eye.

In accordance with one aspect, the present invention is directed to a method for assessing the behavior of a tear film on an ocular surface. The method comprises utilizing optical phase shifting interferometry of a tear film to generate at least one data set and determining the characteristics of the tear film therefrom.

In accordance with another aspect, the present invention is directed to a method for quantitatively assessing the behavior of a tear film on an ocular surface. The method comprises utilizing optical phase shifting interferometry on the ocular surface to generate at least one data set, and analyzing the at least one data set to determine the dynamic characteristics of the tear film over a given period of time.

In accordance with still another aspect, the present invention is directed to a system for assessing the behavior of a tear film on an ocular surface. The system comprises a polarization based interferometer arranged in a Twyman-Green configuration having both a test arm and a reference arm, and at least one simultaneous phase shifting device for capturing images produced by the polarization based interferometer.

Interferometry is a technique which utilizes the behavior of electromagnetic waves in a manner so as to extract information about the path length travelled by the waves. Essentially, in interferometry, electromagnetic waves are superimposed in a manner that will result in an interference pattern that has encoded useful information on the relative length of travel for the interfering waves.

The underlying principle behind interferometry is that when two waves having the same frequency or wavelength combine, the resulting pattern is determined by the phase difference between the two waves. In other words, waves that are in phase will undergo constructive interference while waves that are out of phase will undergo destructive interference.

The anterior refracting surface of the eye is the thin tear film that forms on the surface of and is distributed on the cornea. After blinking, the tear film stabilizes. If, as stated above, no blinking occurs, the tear film normally begins to break up over a time period ranging from about four (4) seconds to about fifteen (15) seconds. An in vivo method of characterizing dynamic tear films has been developed using a near infrared phase-shifting interferometer. This interferometer continuously measures light reflected from the tear film, allowing precision analysis of its dynamic surface topography. Movies showing the tear film behavior may be generated along with quantitative metrics describing the tear film surface as it changes in time. This tear film measurement allows analysis beyond capabilities of typical fluorescein visual inspection or video keratometer and provides better sensitivity and resolution than shearing interferometry methods.

The interferometer of the present invention is capable of identifying features in the tear film less than a micron in height with a spatial resolution of about ten (10) microns over a six (6) mm diameter. The collected surface topographics are analyzed with both traditional optical metrics such as RMS surface deviation and aberration coefficients along with a novel analysis routine used to identify early indications of tear film breakup.

Phase shifting interferometry relies on using data from multiple interferograms to directly measure the phase of a wavefront under test. In one implementation, these interferograms are taken over time. For this specific application the tear film can change between each phase-shifted interferogram, so rapid data collection is required. A second and more preferred embodiment makes use of an instantaneous phase shifting system, where multiple interferograms are recorded concurrently so that there are no changes in the tear film during the data acquisition portion of a measurement. A series of measurements can then record the time-evolution of the tear film.

Static interferometry, on the other hand, relies on tracing the fringe centers of a single interferogram and has lower spatial sampling and lateral resolution than the phase shifting method. Additionally, static interferometry requires additional information to determine the proper wavefront orientation.

In addition to the interferometer, the present system integrates additional modules unavailable in previous technologies. For example, a partial null module and a converger are utilized in the present system and are discussed in detail herein.

The interferometer of the present invention includes a custom optical element in the test arm of the interferometer designed to null the interference pattern that occurs for an "ideal" cornea shape having a 7.8 mm radius of curvature and conic constant of −0.25. Previous technologies used off the shelf camera lenses that do not take this geometry into account and thus their dynamic range is decreased.

It should be noted that the above numbers represent a prolate ellipse in a system where a conic constant of 0 represents a sphere and a conic constant of −1.0 represents a parabola.

The system of the present invention also incorporates a variable null to correct for corneal astigmatism. Most eyes have some level of corneal astigmatism, and without this correction in place, a high fringe frequency could exist even for a "perfect" tear film, reducing the sensitivity and accuracy of the system, along with reducing the overall dynamic range.

In addition to the interferometer, an eye tracker and a fixation target are integrated to stabilize and view eye movements during testing. Safety mechanisms including continuous power monitoring, beam shutters and interlocks are also included in the system to ensure a safe testing environment.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 5 is a series of images developed via blob analysis in accordance with the present invention.

DETAILED DESCRIPTION OF THE PREFERRED EMBODIMENTS

Figure 1:
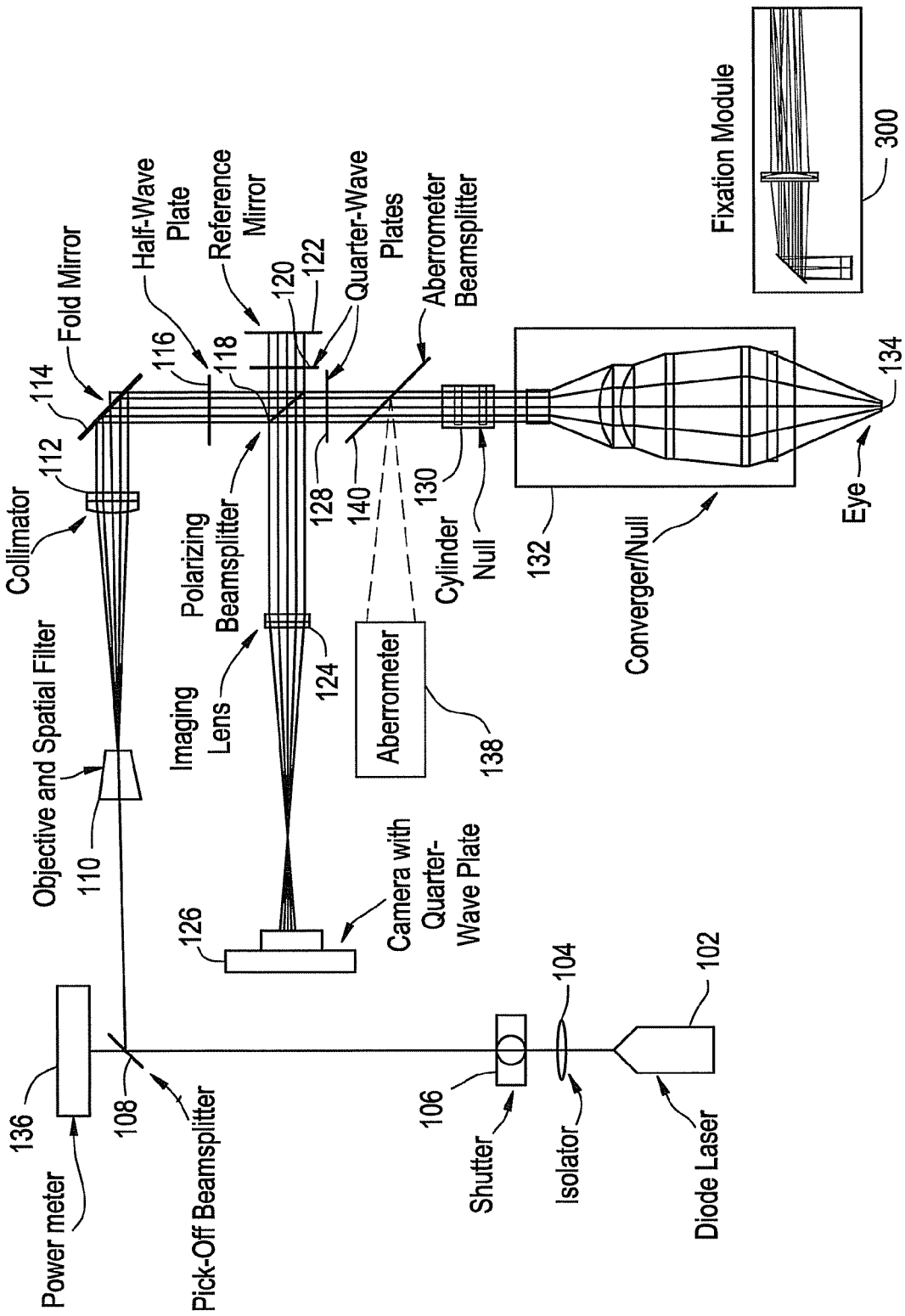
FIG. 1 is a diagrammatic representation of the interferometric system in accordance with the present invention in conjunction with the partial null module.

Phase shifting interferometry relies on using data from multiple interferograms to directly measure the phase of a wavefront under test. In one implementation, these interferograms are taken over time. For this specific application the tear film can change between each phase-shifted interferogram, so rapid data collection is required. A second and more preferred embodiment makes use of an instantaneous phase shifting system, where multiple interferograms are recorded concurrently so that there are no changes in the tear film during the measurement. A series of measurements may then record the time-evolution of the tear film.

The phase shifting interferometer of the present invention provides an in vivo method of evaluating tear film dynamics on a human eye, both with and without contact lenses in place.

In the in vivo system of the present invention, the subject will sit in front of the interferometer and the system will be aligned with the subject's eye. At this point, the system will continuously collect interferometric data for the desired measurement duration. Once the data is captured, algorithms are utilized to convert the phase shifted interferograms into first phase information and that phase information is then converted into a single surface measurement. This process is repeated for each measurement. The measurements are compared to determine how the tear film has changed over time. There are a number of ways of analyzing the data set of surface measurements and it is expected that other ways will suggest themselves to those skilled in the relevant art without departing from the spirit and scope of the invention.

A first method is to just examine the unaltered or unedited measurements without any modification thereto. The unaltered or unedited measurements refer to the surface contour with only piston and tilt subtracted from the information. Statistics describing the surface may be captured for each measurement frame and output to a database as needed.

A second method relies on subtracting one "reference" frame from every measurement and analyzing that output. By referencing every measurement to one within the set, the changes in the tear film shape are easily seen and analyzed. In other words, any systematic or constant characteristics are filtered out. In one exemplary embodiment, the first collected surface is utilized as the reference surface. In an alternate exemplary embodiment, the surface corresponding to the time after blink, yielding the most stabile vision, (approximately one to two seconds after blink) is utilized as the reference surface. In yet another alternate exemplary embodiment, the most stable surface in the set, as determined by a particular metric, for example, RMS, is used as the reference surface.

A third method relies on subtracting a fitted polynomial surface from each measurement. This differs from the second method described above in that the reference surface being subtracted now changes for each measurement. By doing this, only the high order surface perturbations are seen. It is thought that tear film break-up happens in a way that may not be described by simple polynomials, so subtracting such a surface makes those features easily identifiable.

In all the above described methods, software scripts or algorithms are used to modify, analyze and save the desired data. Statistics may be saved to a database, and the visual surface representations may be combined to create a movie of the tear film evolution over time.

In a preferred exemplary embodiment, the interferometer is a custom built polarization based Twyman-Green system where the patient is seated such that his or her eye is positioned in a test arm of the system. The preferred exemplary embodiment is illustrated in diagrammatic format in FIG. 1. In an alternate exemplary embodiment, the interferometer may be built on a laser Fizeau configuration; however, as stated above, the Twyman-Green system is preferred because of its ability to more easily phase shift using the single shot method. In addition, the polarizing variant more easily allows adjustment of laser power into each arm of the interferometer, allowing testing over a large range of reflectances. A beam expander and converger system is used in the test arm to expand the beam and focus it at the center of curvature of the tear film. In this method, the test beam is reflected back through the system where it is combined with a reference beam and directed to a camera. The resulting interference pattern between the two signals is used to calculate the phase of the wavefront reflected off of the tear film and this information may be used to calculate a topographic map of that surface.

The light source 102 is a stabilized diode laser with a wavelength of 785 nm. This wavelength is desirable since it appears as a very dull light to most humans. Therefore, the tear film will not be altered by a bright signal causing discomfort and potentially producing reflex tearings. The light from the diode laser 102 is passed through an isolator or a neutral density filter 104, a high speed shutter 106, a pick-off beam splitter 108, an objective and spatial filter 110 and a collimator 112 wherein it is spatially filtered and expanded to an eighteen (18) mm diameter collimated beam. This beam is then directed to a fold mirror 114 and passes through a half-wave plate 116 which allows the intensity in the test and reference arms to be balanced, and is split into each arm with a polarizing beam splitter cube 118. In the reference arm, the beam passes through a quarter-wave plate 120, oriented with its fast axis at forty-five (45) degrees, is reflected off a reference mirror 122, and again passes back through the quarter-wave plate 120 to the polarizing beam splitter cube 118 where it is directed toward a camera 126, discussed in detail subsequently, through an imaging lens 124 and quarter-wave plate oriented with its fast axis at forty-five (45) degrees (not shown) associated with the camera 126. In the test arm, the beam passes through a quarter-wave plate 128 oriented with its fast axis at forty-five (45) degrees, through an aberrometer beam splitter 140, a partial null module 130, discussed in detail subsequently, through a beam expander and converger 132, discussed in detail subsequently, and is reflected off the tear film in the eye 134. The beam then passes back through the beam expander and converger 132, the partial null module 130, the aberrometer beam splitter 140, the quarter-wave plate 128, the polarizing beam splitter cube 118, the imaging lens 124, the quarter-wave plate and into the camera 126. The aberrometer beam splitter 140 directs a portion of the beam to a wavefront aberrometer 138, which is discussed in detail subsequently.

It is important to note that both the reference and test beams pass through an imaging lens 124 which images the tear film onto the camera. The beams pass through an additional quarter-wave plate associated with the camera 126.

The camera 126 or detector in the system is a Pixelated Camera Kit available from 4D Technology Corporation. This camera 126 comprises a CCD where a pixilated phase mask is aligned to the sensor. The purpose of the phase mask is to create four phase shifted interferograms on a single detector. In this way, instantaneous phase shifting inteferometry may be used to measure the dynamic tear film. Alternately, there are simultaneous phase shifting systems that utilize multiple cameras and polarizers. In addition, the simultaneous system may be replaced with high speed cameras and rapid phase shifting. In other words, any suitable means for capturing the images may be utilized in conjunction with any suitable means for phase shifting.

The main purpose of the converger 132 is to focus the laser at the center of curvature of the tear film, ensuring that the reflected signal follows the proper path back towards the camera 126. The specific design of the converger 132 is driven by the desired diameter to be tested on the contact lens or eye tear film, along with the working distance between the contact lens or eye tear film and the converger. The image space f/# of the converger 132 must be less than or equal to the tear film radius of curvature divided by the test diameter, represented by the equation $$f/\# = R_{tear\,film}/D_{test}.$$

As the desired test area increases, the f# must become smaller. Assuming a constant working distance, this means the lens diameter must become larger as well. In general, increasing the working distance or increasing the test area also increases the converger diameter. Therefore, the desired test geometry must be balanced with practical manufacturing considerations.

Additionally, the effective f/# of the entire imaging system, including both the converger and the imaging lens must be sufficient to match the resolution of the camera. The cutoff frequency of the detector is the largest fringe frequency it is capable of resolving (i.e., smallest fringe spacing). The cutoff frequency of the imaging system is the largest frequency it is capable of transmitting through to the detector. The limiting detector resolution is given by the equation $$\xi_{Detector} = 1/(2 * d_{pixel}),$$

where $d_{pixel}$ is the pixel pitch on the detector. The imaging lens cutoff frequency or wavelength is given by $$\xi_{Imaging} = 1/(\lambda * f/\#_w),$$

where $\lambda$ is the wavelength and $f/\#_w$ is the working, or effective, f/# of the imaging system. In order to achieve a detector limited system, which is preferable, the imaging lens cutoff frequency must be larger than the detector cutoff frequency.

In the exemplary embodiment of the invention, the converger 132 was designed to test a six (6) millimeter diameter area on the eye and provide a working distance of seventy-seven (77) millimeters between the last element of the converger and the eye, and assumes nominal surface geometry with 7.8 millimeter radius of curvature and a conic constant of −0.25. Based on these requirements, the image space f/# of the system must be 1.4 or faster and more preferably 1.33 or faster.

In addition to focusing the beam at the tear film's center of curvature, the converger 132 must also take into account the conic shape of the cornea. Since the beam is reflected off of this conic surface back into the interferometer, many fringes would be observed if the conic shape of the cornea is not taken into account.

Figure 2:
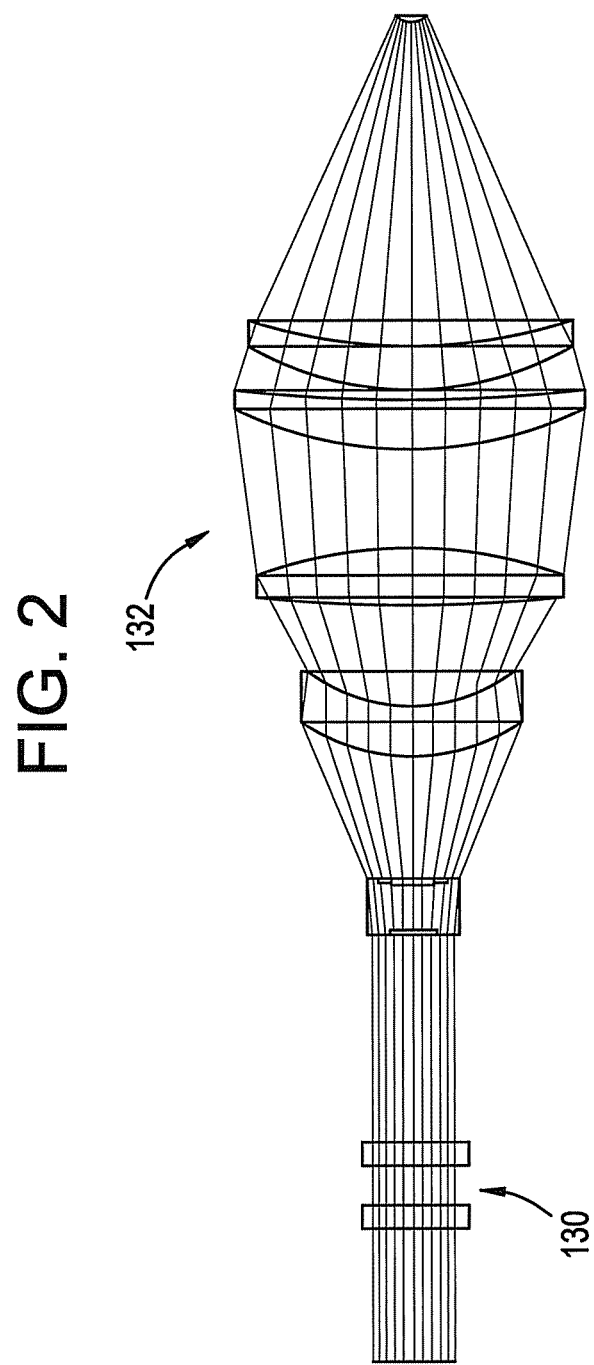
FIG. 2 is a diagrammatic representation of the converger optics in conjunction with the partial null module in accordance with the present invention.

In the exemplary system, beam expanding optics are also incorporated into the converger system in order to provide a large enough beam to achieve the required f/# and working distance. The optics first expand an input beam having a diameter of eighteen (18) millimeters and then bring it to a focus as the proper location. The beam is reflected off of the tear film before it actually reaches focus and travels back through the converger following its previous path in reverse. The length of the system from first to last lens is one hundred forty (140) mm and the largest element diameter is eighty-two (82) mm. FIG. 2 is a diagrammatic representation of both the converger 132 and the partial null module 130, which is shown to the left of the converger 132 in the drawing.

The partial null module 130 within the interferometer corrects for corneal astigmatism that will likely be present in the eyes under test. Corneal astigmatism occurs when the cornea's radius of curvature varies along different planes. If not taken into account, the measurements will show astigmatism which may introduce overall measurement errors.

To correct this, the opposite amount of astigmatism may be introduced into the system. This is done by using a pair of cylinder lenses with opposite radii of curvature in collimated space before the converger. When these lenses are rotated with respect to each other and the whole system, the proper amount of astigmatism can be introduced without added other aberrations to the system. Essentially, the cylinder lenses work in the same manner as the cylindrical corrections in spectacles or contact lenses.

In the partial null module 130, the first cylinder lens is plano-concave with the concave side having a radius of 1500 mm. The second cylinder lens is plano-convex with the convex side having a radius of 1500 mm. Each is made of BK7 glass and has a center thickness of five (5) mm. Each lens is mounted in a rotation mount, and they are located ten (10) mm apart. FIG. 2 illustrates these lenses, although the concave/convex surfaces appear mostly flat due to the long radius. When rotated as described, these lenses provide continuously variable corneal astigmatism accommodation providing up to roughly +/−1.3 diopters of dynamic range.

In interferometry it is crucial to stabilize the surface under test. Therefore, a sturdy chin rest and head rest will be used to stabilize the subject. Once the person is stable in this mount, the system may then be accurately aligned to the eye.

In order to keep the eye steady, a fixation system or module 300 is used. This fixation system presents a collimated signal to the opposite eye under test. For example, if measuring the tear film on the left eye, the fixation target will be presented to the right eye. By asking the subject to focus on this target, eye movement will stabilize. By moving the target, the gaze direction of the subject can also be changed.

Figure 3:
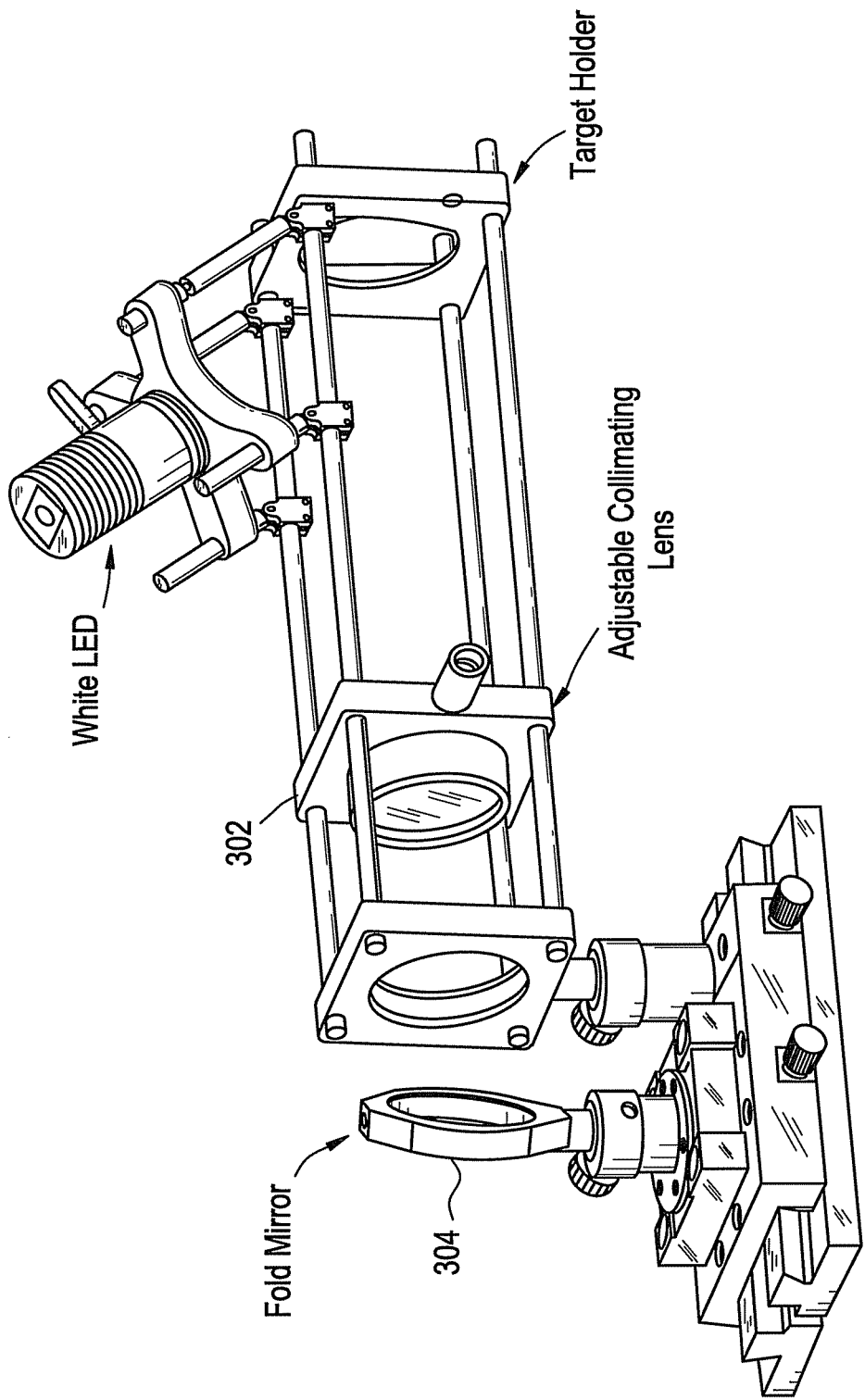
FIG. 3 is a diagrammatic representation of the optical layout of the fixation module in accordance with the present invention.
Figure 4:
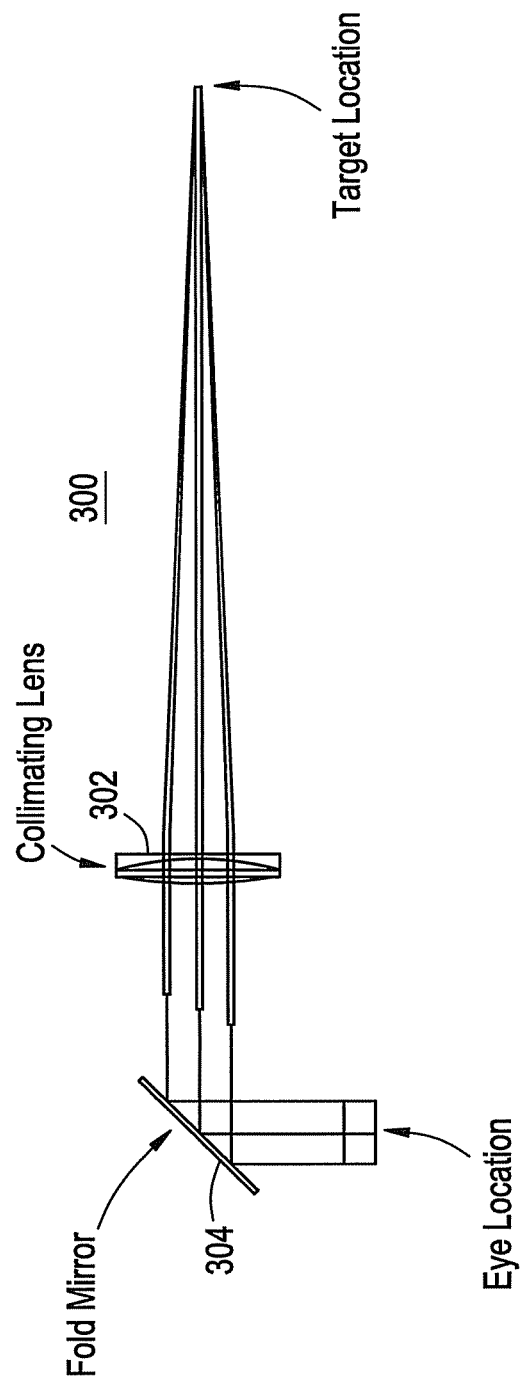
FIG. 4 is a diagrammatic representation of the mechanical layout of the fixation module in accordance with the present invention.

The optical system comprises a target, collimating lens 302 and fold mirror 304. The target is adjusted to provide targets of differing visual angles or geometries. The collimating lens 302 may be adjusted by the user to adjust proper focus taking into account the patient's vision. FIG. 3 and FIG. 4 illustrate the optical and mechanical designs of the fixation module 300.

The system or module 300 also integrates an off-the-shelf eye tracking system to track eye movements and ensure that changes observed in the measurements are the result of tear film changes and not eye movement. The supplier of this system is Arrington Research.

The laser 102 included in the system normally operates at class 3B, which may not be eye safe. Unfortunately, low power sources at the desired stabilized wavelength are not commercially available so the optical power in the system must be reduced to safe levels. A variable neutral density filter is used to set the output power, and a pick-off mirror or pick-off beam splitter 108 (see FIG. 1) is used to continuously monitor the power output via a power meter 136 (see FIG. 1). Interlocks are used to ensure the power is not altered once set at safe levels. If these interlocks are broken, the system shuts down.

While the measured fluid layer surfaces may be described with traditional optical metrics such as RMS surface height or aberration terms, these metrics do not adequately describe the fluid layer topography. Features such as pits in the tear film are an early indication of tear film breakup, and their presence is not quantified with the aforementioned metrics. It is important to know precisely when and where these artifacts begin. The presence of these artifacts in the tear film indicates the tear film is beginning to degrade, which on the eye can cause discomfort or vision degradation. Therefore, a "blob analysis" routine was developed to analyze the measurements in order to identify and quantify holes or pits in the tear film. Blob analysis is a simple form of texture analysis and generally involves various methods of extracting textural features from images. It is important to note that the analysis is preferably done over multiple and differently sized apertures because a stated RMS value for a given measurement aperture may be arrived at by surfaces that might be characterized as smooth or rough. Multiple measurements over different aperture sizes are thus needed to remove the ambiguity, to better determine the spatial frequencies of the surface within the test aperture.

FIG. 5 shows the four major steps in the blob analysis routine developed in conjunction with this instrument. The first step of the blob analysis procedure is to import the surface measurement into IDL (ITT Visual Information Solutions, Boulder, Colo.). In step two an un-sharp mask is applied to the measurement which effectively amplifies the high frequency areas on the surface corresponding to the perimeter of the blobs. The original measurement is then subtracted from the unsharp masked version leaving data only at those areas enhanced by the unsharp mask, and a smoothing kernel applied to remove noise, leaving only areas of interest (the blobs) in the fluid layer visible. At this point (end of step 3) the processed measurement is a binary data array consisting of high values where the blob exists and low values everywhere else. In the final step perimeters are fit to every individual blob and the number of blobs along with their areas and locations are recorded.

Other methods of analysis include wavelet analysis, fractal analysis and Fourier Transform analysis.

In accordance with another aspect, a wavefront aberrometer may be utilized in combination with the tear film interferometer of the present invention. A wavefront aberrometer is a diagnostic instrument which utilizes wavefront technology to measure wavefront errors or aberrations (optical imperfections, both low and high order) of the eye. In this case, the aberrations measured would include any imperfections in the eye, the contact lens and the tear film. In the exemplary embodiment illustrated in FIG. 1, the wavefront aberrometer 138 is synchronized to the operation of the interferometer such that both changes in the surface of the tear film interferometry and the corresponding changes to the ocular wavefront may be collected. An aberrometer beam splitter 140 is positioned between quarter wave plate 128 and the cylinder null 130. In order for the aberrometer 138 to be used in conjunction with the tear film interferometer, appropriate optical elements must be provided in the aberrometer 138 so that the separate aberrometer light source produces a collimated beam at the eye 134. The combination of tear film interferometry and wavefront aberrometry has the benefit of being able to attribute a portion of the changes in the wavefront to the tear film. More specifically, the data may be utilized to differentiate or compare tear film changes versus changes due to contact lens movement.

This information may then be utilized to optimize the design of the contact lens. For example, two major components of temporal changes to the ocular wavefront are typically the tear film and contact lens movement. Without the combination of an interferometer and aberrometer, there is currently no way of separating the two factors. In a preferred exemplary embodiment, a fiducialized contact lens is utilized to track contact lens position. Essentially, a fiducial in optics is an object used in the field of view of an imaging system which appears in the image produced and is used as a point of reference. Contact lens position; namely, centration and rotation, is encoded in the wavefront aberrometer's data via the shadow cast by the fiducials of the contact lens.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A method for assessing the behavior of a tear film on an ocular surface comprising utilizing optical phase shifting interferometry of a tear film to generate at least one data set and analyzing the characteristics of the tear film therefrom, wherein the at least one data set is converted into first phase information which is subsequently converted into a first single surface measurement; repeating the conversion for each data set; and comparing the surface measurements to determine how the tear film has changed over time.

2. The method for assessing the behavior of a tear film on an ocular surface according to claim 1, wherein the ocular surface is a tear film over a cornea of an eye.

3. The method for assessing the behavior of a tear film on an ocular surface according to claim 1, wherein the ocular surface is a tear film over a contact lens.

4. The method for assessing the behavior of a tear film on an ocular surface according to claim 1, wherein the step of analyzing comprises examining the surface measurements with only piston and tilt subtracted from the data utilized to create the surface measurements.

5. The method for assessing the behavior of a tear film on an ocular surface according to claim 1, wherein the step of analyzing comprises subtracting a reference surface from each of the surface measurements.

6. The method for assessing the behavior of a tear film on an ocular surface according to claim 5, wherein the reference surface is a fitted polynomial surface.

7. The method for assessing the behavior of a tear film on an ocular surface according to claim 5, wherein the reference surface is one of the individual surface measurements.

8. A method for quantitatively assessing the behavior of a tear film on an ocular surface, the method comprising:
utilizing optical phase shifting interferometry on the ocular surface to generate at least one data set; and
analyzing the at least one data set to determine the dynamic characteristics of the tear film over a given period of time, wherein the at least one data set is converted into first phase information which is subsequently converted into a first single surface measurement; repeating the conversion for each data set; and comparing the surface measurements to determine how the tear film has changed over time.

9. The method for quantitatively assessing the behavior of a tear film on an ocular surface according to claim 8, wherein the ocular surface is a tear film over a cornea of an eye.

10. The method for quantitatively assessing the behavior of a tear film on an ocular surface according to claim 8, wherein the ocular surface is a tear film over a contact lens.

11. The method for quantitatively assessing the behavior of a tear film on an ocular surface according to claim 8, wherein the step of analyzing comprises examining the surface measurements with only piston and tilt subtracted from the data utilized to create the surface measurements.

12. The method for quantitatively assessing the behavior of a tear film on an ocular surface according to claim 8, wherein the step of analyzing comprises subtracting a reference surface from each of the surface measurements.

13. The method for quantitatively assessing the behavior of a tear film on an ocular surface according to claim 12, wherein the reference surface is a fitted polynomial surface.

14. The method for assessing the behavior of a tear film on an ocular surface according to claim 12, wherein the reference surface is one of the individual surface measurements.

15. The method for quantitatively assessing the behavior of a tear film on an ocular surface according to claim 8, further comprising texture analysis on the at least one data set.

16. The method for quantitatively assessing the behavior of a tear film on an ocular surface according to claim 15, wherein the texture analysis comprises blob analysis.

17. The method for quantitatively assessing the behavior of a tear film on an ocular surface according to claim 8 further comprising collecting wavefront aberrometry data and comparing this data to the surface measurements for each data set to differentiate tear film changes.

18. The method for quantitatively assessing the behavior of a tear film on an ocular surface according to claim 17 further comprising collecting wavefront aberrometry data and comparing this data to the surface measurements for each data set to differentiate tear film changes versus contact lens movement.

* * * * *